United States Patent
Martis et al.

(10) Patent No.: US 7,683,759 B2
(45) Date of Patent: Mar. 23, 2010

(54) PATIENT IDENTIFICATION SYSTEM

(75) Inventors: Dinesh J. Martis, Loveland, OH (US); Edward S. Biggins, Cincinnati, OH (US); Frederick M. Oehler, Goshen, OH (US); Lawrence G. Smith, Cincinnati, OH (US); Olivier Fischer, Madeira, OH (US); Jason C. Hispkind, Fishers, IN (US); George P. Jones, Fishers, IN (US)

(73) Assignee: Martis IP Holdings, LLC, Cincinnati, OH (US)

( * ) Notice: Subject to any disclaimer, the term of this patent is extended or adjusted under 35 U.S.C. 154(b) by 489 days.

(21) Appl. No.: 10/959,660

(22) Filed: Oct. 6, 2004

(65) Prior Publication Data

US 2006/0074280 A1     Apr. 6, 2006

(51) Int. Cl.
*G05B 19/00* (2006.01)
*G06F 7/00* (2006.01)
*G06T 1/00* (2006.01)
*H04B 1/00* (2006.01)

(52) U.S. Cl. .................. 340/5.83; 340/5.82; 340/5.74; 340/532; 705/3

(58) Field of Classification Search ........... 340/5.82, 340/5.8, 5.51–5.54, 286.07, 5.83, 5.74, 532; 235/382, 382.5, 115, 375; 600/323, 333; 128/672, 661.08; 705/3; 382/124, 118, 115
See application file for complete search history.

(56) References Cited

U.S. PATENT DOCUMENTS

| | | | |
|---|---|---|---|
| 5,193,855 A | 3/1993 | Shamos | |
| 5,309,916 A * | 5/1994 | Hatschek | 600/485 |
| 5,381,487 A | 1/1995 | Shamos | |
| 5,719,950 A | 2/1998 | Osten | |
| 5,737,539 A | 4/1998 | Edelson | |
| 5,758,095 A | 5/1998 | Albaum | |
| 5,822,741 A | 10/1998 | Fischthal | |
| 5,833,599 A | 11/1998 | Schrier | |
| 5,845,255 A | 12/1998 | Mayaud | |
| 5,876,926 A | 3/1999 | Beecham | |
| 5,879,453 A | 3/1999 | Streeter et al. | |
| 5,991,731 A | 11/1999 | Colon | |
| 6,012,034 A | 1/2000 | Hamparian | |
| 6,047,259 A | 4/2000 | Campbell | |
| 6,088,585 A | 7/2000 | Schmitt | |
| 6,094,589 A | 7/2000 | Schmitt | |
| 6,141,436 A | 10/2000 | Srey | |
| 6,154,726 A | 11/2000 | Rensimer | |
| 6,181,808 B1 | 1/2001 | Fukuzumi | |
| 6,224,548 B1 * | 5/2001 | Gopinathan et al. | 600/300 |
| 6,314,384 B1 | 11/2001 | Goetz | |
| 6,317,719 B1 | 11/2001 | Schrier | |
| 6,406,426 B1 * | 6/2002 | Reuss et al. | 600/300 |
| 6,418,235 B1 * | 7/2002 | Morimoto et al. | 382/118 |
| 6,421,650 B1 | 7/2002 | Goetz | |

(Continued)

*Primary Examiner*—Brian A Zimmerman
*Assistant Examiner*—Nam V Nguyen
(74) *Attorney, Agent, or Firm*—Porter Wright Morris & Arthur LLP

(57) ABSTRACT

A patient identification device is disclosed. The device includes a first sensor, a second sensor, and a processor. The first sensor may be configured to be positioned on the patient's finger. The device may include a camera. The device may include an identifier. The identifier displays a randomly generated alphanumeric code for further identification of the patient.

21 Claims, 1 Drawing Sheet

U.S. PATENT DOCUMENTS

| | | | |
|---|---|---|---|
| 6,537,225 B1 | 3/2003 | Mills | |
| 6,643,531 B1 | 11/2003 | Katarow | |
| 6,669,086 B2 * | 12/2003 | Abdi et al. | 235/379 |
| 6,684,093 B2 * | 1/2004 | Kuth | 600/407 |
| 6,687,676 B1 | 2/2004 | Denny | |
| 6,697,783 B1 | 2/2004 | Brinkman | |
| 6,711,547 B1 | 3/2004 | Glover | |
| 6,738,754 B1 | 5/2004 | Norman, Jr. | |
| 6,757,408 B2 * | 6/2004 | Houvener | 382/115 |
| 6,819,783 B2 * | 11/2004 | Goldberg et al. | 382/115 |
| 6,820,057 B1 | 11/2004 | Loch | |
| 6,824,052 B2 | 11/2004 | Walsh | |
| 6,937,135 B2 * | 8/2005 | Kitson et al. | 340/5.52 |
| 6,991,155 B2 * | 1/2006 | Burchette, Jr. | 235/379 |
| 7,069,444 B2 * | 6/2006 | Lowensohn et al. | 713/185 |
| 7,074,183 B2 * | 7/2006 | Castellanos | 600/300 |
| 7,125,335 B2 * | 10/2006 | Rowe | 463/25 |
| 7,230,519 B2 * | 6/2007 | Coughlin et al. | 340/5.82 |
| 2002/0002473 A1 | 1/2002 | Schrier | |
| 2002/0032387 A1 * | 3/2002 | Geva et al. | 600/538 |
| 2002/0042725 A1 | 4/2002 | Mayaud | |
| 2002/0042726 A1 | 4/2002 | Mayaud | |
| 2002/0087533 A1 | 7/2002 | Norman, Jr. | |
| 2002/0125991 A1 | 9/2002 | Levin | |
| 2003/0144884 A1 | 7/2003 | Mayaud | |
| 2003/0199945 A1 * | 10/2003 | Ciulla | 607/48 |
| 2004/0107117 A1 | 6/2004 | Denny | |
| 2004/0190759 A1 | 9/2004 | Caldwell | |
| 2004/0213440 A1 * | 10/2004 | Joo et al. | 382/124 |
| 2005/0078851 A1 * | 4/2005 | Jones et al. | 382/100 |

* cited by examiner

PATIENT IDENTIFICATION SYSTEM

FIELD OF THE INVENTION

The present invention relates generally to an identification system, and more specifically relates to an identification system that can be used in the medical or healthcare industry.

BACKGROUND OF THE INVENTION

In the healthcare industry, test are often administered in order to classify a patient with a certain condition or to qualify a patient for a certain treatment. Such a test may be administered by a physician, but often is administered by a technician. The technician may be under the employment of a hospital or doctor's office, or in the alternative, may be under the employment of a third party that has an interest in servicing the potential patient. It is in these latter situations that it becomes particularly important to have a fail-safe test administration method with safeguards against fraud. However, of course, such an identification system may be used in a number of situations, and is not restricted to those scenarios described.

The following is one example of how the current process works to order oxygen treatment for a patient. The patient visits a physician. The physician will take a patient history and will determine a diagnosis and determines the need for a patient to have oxygen treatment. In most cases a patient will tell the physician they are experiencing shortness of breath or some other oxygen related ailment. The physician may ask the patient to take a pulse oximetry test to determine if they are in need of oxygen treatment. If the patient pulse oximetry test shows that the patient is in need of oxygen treatment the physician will prescribe oxygen for the patient. To be reimbursed via a payor source (insurance company, Medicare, Medicaid, etc.), a third party Independent Diagnostic Testing Facility must test the patient and submit the test results to the physician. The physician must submit a CMN (Certificate of Medical Necessity) along with the patient's test results to the payor source for reimbursement.

Identification means in such a scenario are known in the art. For example, U.S. Pat. No. 6,643,531 to Katarow discloses a combination fingerprint and oximetry device. U.S. Pat. No. 5,719,950 to Osten, et al. discloses a biometric, personal authentication system. Other patents and publications that may be of relevance include: U.S. Pat. No. 6,537,225, U.S. Pat. No. 6,181,808, U.S. Pat. No. 6,141,436, U.S. Pat. No. 6,094,589, U.S. Pat. No. 6,088,585, U.S. Pat. No. 5,876,926, and U.S. Patent Application No. 2002/0125991.

Despite the testing and identification procedures known in the art, potential for fraud exists in the pulse oximetry business. Healthcare groups such as Medicare have established that they will reimburse for oxygen required by any patient whose pulse oximetry test results fall below the threshold of 89%. Because pulmonary disease is degenerative and never improves, under current Medicare standards, once a qualifying reading has been taken on a patient, that patient is considered a candidate for oxygen for the rest of their life. Clearly, it is in the interest of a provider of oxygen that its patients have qualifying readings.

In an effort to establish that a patient has a pulse oximetry below the threshold of 89%, some test administrators may have submitted test results from other patients that are known to be below the threshold, thereby falsifying the records, rather than submitting the test results of the actual patient that may not fall below the threshold. Such falsification and fraud before payor sources (i.e. Medicare, Medicaid, third party payor sources, etc.) could be eliminated with a sufficient patient identification system in place.

SUMMARY OF THE INVENTION

The present invention relates to one or more of the following features, elements or combinations thereof. A patient identification device can include a patient identifier, a processor, a pulse oximeter, a camera, and an alphanumeric display. As used herein, alphanumeric comprises any combination of numbers, letters, or other indicators that can be used. Positive identification of the patient may be made in any number of ways (and combinations of ways), including fingerprint identification, retinal identification, other biometric identification, pulse comparison, patient identity comparison with central data repository, visual identification via a camera, and visual identification by the physician. As used herein, the term "biometric" refers to any statistic or observation relating to a living body.

The present invention also provides methods for continual or intermittent identification of the patient during the testing procedure. Such identification ensures that the same patient is being tested during the entirety of the procedure.

Additional features of the invention will become apparent to those skilled in the art upon consideration of the following detailed description of preferred embodiments exemplifying the best mode of carrying out the invention as presently perceived.

DETAILED DESCRIPTION OF EMBODIMENTS OF THE INVENTION

Figure 1:
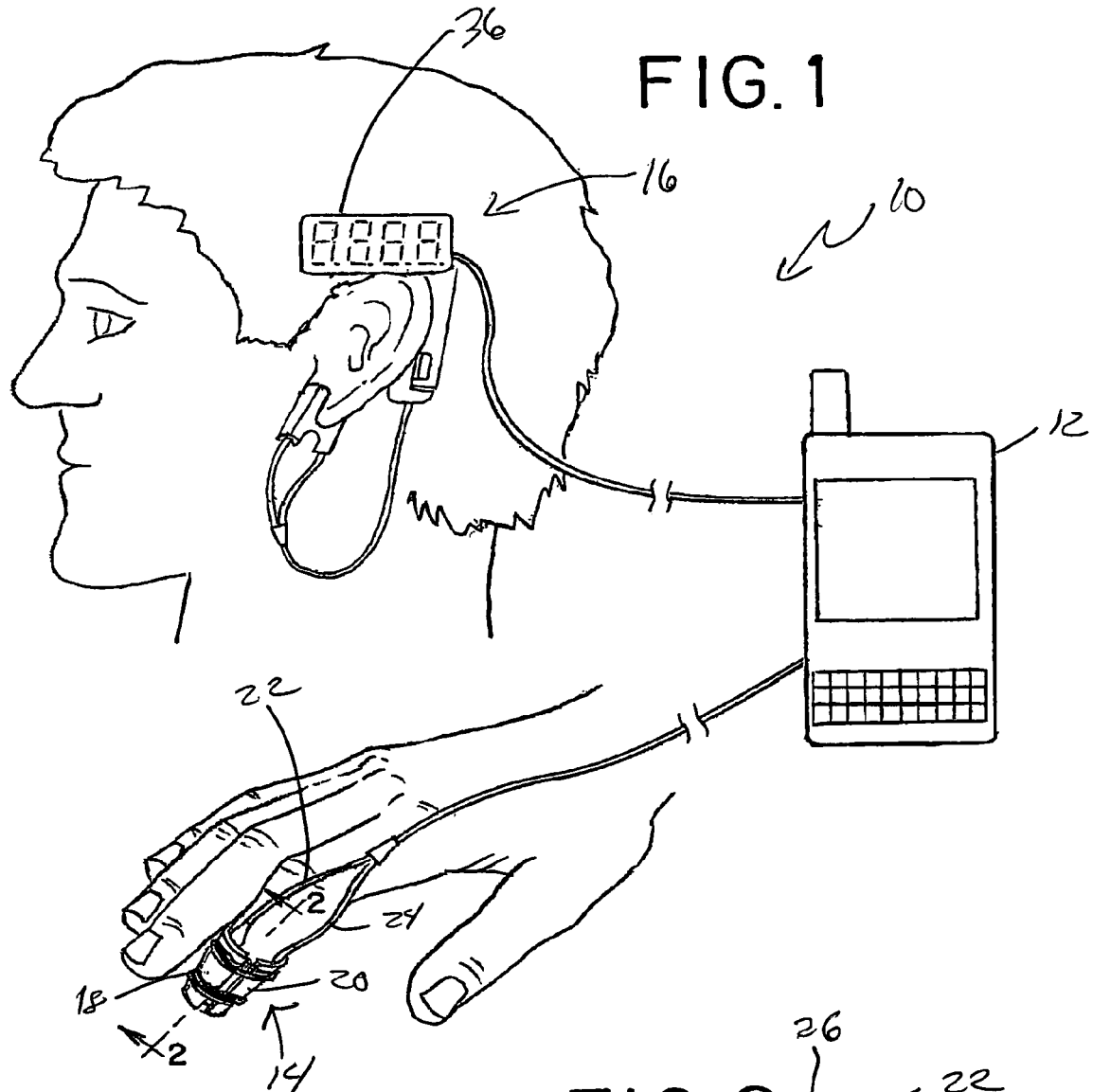
FIG. 1 is a perspective view of an identification system used to identify a patient during a testing procedure.

As can be seen in FIG. 1, a patient identification system 10 comprises a portable processor 12, a first sensor 14, and a second sensor 16. Illustratively, portable processor 12 is a personal digital assistant (PDA), as shown. First sensor 14 can be a finger clip having any one of a pulse oximeter, fingerprint identifier, or other biometric sensor. Second sensor 16 is illustratively an ear sensor that provides secondary identification means, such as a second biometric sensor. However, it should be understood that second sensor 16 can be positioned in any number of places, identifying the patient in any number of ways known in the art. The following description discusses on embodiment that can be useful in identifying a patient and securely taking the pulse oximetry of the identified patient. However, many other embodiments are within the scope of the claims, and a person skilled in the art will understand that the patient identification system disclosed can be modified and still provide secure results as contemplated by this invention.

Figure 2:
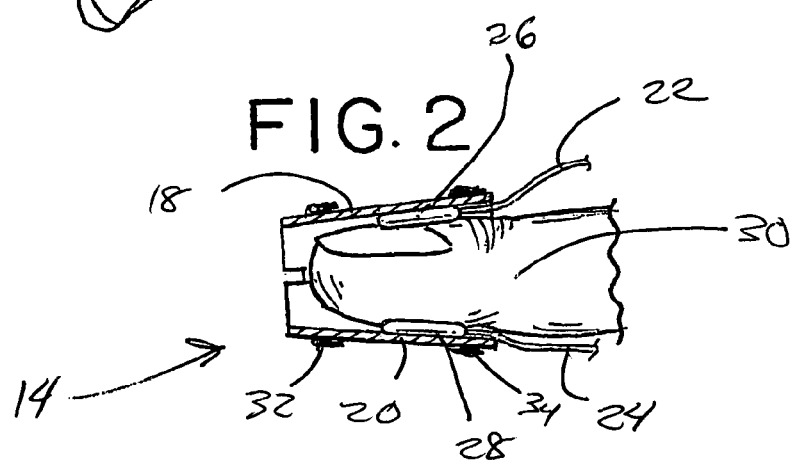
FIG. 2 is a perspective view of one embodiment of a finger sensor.

Patient identification system 10 illustratively can be comprised of the following elements. The first sensor 14 can record pulse oximetry data by utilizing a sensor or other device that records the percentage of haemoglobin (Hb) that is saturated with oxygen. The sensor may consist of a wire with two ends that can be looped around a finger, ear lobe or other relevant body part to record oximetry information. The wire (sensor) can be encased in any number of materials to make it convenient for a patient to hold the sensor firm on the finger or other body part. Any material such as soft rubber material, plastic, adhesive tape, fabric, Velcro fastener material and or any other material suitable for holding the sensor in position on the finger or other body part may be used. Illustratively, as can be seen in FIGS. 1 and 2, sensor 14 comprises first and second arcuate plates 18, 20, each having a wire 22, 24 leading to a contact portion 26, 28 positioned between the respective plates 18, 20 and a patient's finger 30. Contact portions 26, 28 may comprise rubber, metal, adhesive, or any other material known in the art.

Plates 18, 20 are illustratively connected with straps 32, 34, which may be Velcro® or any other material suitable to connect plate 18 to plate 20, positioning a portion of the finger 30 therebetween. The first sensor 14 may also record heart rate information.

A second sensor 16 may be placed on the patient at a separate place from the first. This sensor is designed to record heart rate information at precisely the same time as the first sensor. This information is used for comparison purposes to further confirm that the readings are associated with the appropriate patient. A different heart rate (or no heart rate . . . if the sensor is not attached properly) will lead to an inaccurate report and will disqualify the testing.

Additionally second sensor 16 can display a randomly generated identifier (illustratively generated by portable processor 12), displayed by LED or LCD 36, shown in FIG. 1. Such an identifier displayed by LCD 36 can be photographed by a camera (not shown, but could be incorporated with portable processor 12) to further validate the identity of the patient. One method of use would be to photograph the patient and the LCD 36 together, similar to the view shown in FIG. 1, so as to identify the patient by physical and biometric characteristics. This LCD identifier, and the profile of the patient, will also be intermingled with the patient test results for comparison purposes with the visual display in the photograph. These safeguards allow for unique identification of the appropriate patient. Combined with the biometric and heart rate information from the other components of this system, it becomes virtually impossible for any person or group to submit incorrect results for a patient.

Portable processor 12 may utilize different chipsets that can be combined to accumulate and process all of the different patient results for each particular test. One chipset may be used for all data processing or multiple chipsets may be used to accomplish the same goal. An illustrative chipset is manufactured by Masimo Corporation and can be found at http://www.masimo.com/oem/oem.htm.

The first sensor 14 may use infrared LED to measure deoxygenated hemoglobin. Such an infrared LED may be purchased from AuthenTec in Cincinnati, Ohio. An example of an ear clip that can be used in the system is manufactured by Nellcor and can be found at http://shop.medical.philips.com/phstore/catalog/details.asp?product=M1194A(PMS_CMS_90)&view=image.

Patient identification system 10 also can have the capability to remotely connect and transmit all patient data recorded during a session or multiple sessions. The system can connect via any number of methods including standard POTS line (Plain Old Telephone System), broadband, LAN, WAN, Intranet, Extranet, VPN, etc. Once connected the system has the ability to 'push' or 'pull' data. The system can remotely purge data from the remote unit once it has been transmitted to the central data repository. Portable processor 12 may be equipped with such a communication device, or may connect to such a communication device in order to transmit information.

A central data repository houses all of the patient data (biometric, heart rate, relevant patient data such as name, doctor, address, etc.) and the associated readings from the pulse oximetry tests (or other relevant tests). When a new test is complete and ready to transmit, the data is first checked against all patient data already existing in the central repository for uniqueness. One of two cases will occur. First, if the system is expecting to receive new test results for an existing patient, the system will check the central data repository and will match the incoming patient data (biometric) with the existing patient data in the central data repository. Alternatively, if the system is not expecting new results for an existing patient (ie; the patient has already submitted qualifying results) and the system detects duplicate patient data (biometric) on new test results, the results will be deemed ineligible or disqualified and will not be accepted into the system. Additionally, a flag will be set for administrators to watch results being submitted by the party who submitted the false results. The data housed in the central data repository will allow for specific matching of patient records to patients without question and will provide a method to immediately detect any duplicate or false submissions.

The central data repository can be accessible via any number of methods. The portable processor 12 can directly dial into a bank of modems that will answer the calls and begin a communication routine to verify, validate, accept/reject, transmit and terminate the transaction. The portable processor 12 can also communicate via other data connections such as the Internet, LAN, WAN, VPN, etc. Once connected the remote units can transmit data to the central repository. The remote units can either purge or save the patient data on the remote unit once data transmission has occurred.

Biometric information is illustratively read and integrated with the pulse oximetry data. This combined data represents a uniquely identifiable dataset for each individual. Biometric information can be read with the use of a biometric sensor, such as second sensor 16, that may be incorporated or may be separate from the pulse oximeter sensor. Biometric information may also be read with finger sensor 14. Illustratively, second sensor 16 is an ear clip capable of taking the pulse of the patient. Any method of attachment to the individual patient may be utilized (soft rubber material, plastic, adhesive tape, fabric, Velcro fastener material and or any other material suitable for holding the sensor in position on the finger or other body part may be used). If the second sensor is utilized as a separate device then alternative means to incorporate biometric data may be used (retinal scan, voice recognition, facial recognition, etc.) or fingerprint biometric data may be collected in a different manner (hand scanner, separate finger probe, etc.). Regardless of what biometric information is used and/or how the biometric information is collected, it can be incorporated with the pulse oximeter data to uniquely identify each individual patient.

Portable processor 12 can be configured to read biometric information (fingerprint, retinal scan, etc.) on a continuous or intermittent basis and inter-mingle the biometric data with pulse oximetry readings (or other relevant readings depending on the test being performed) from a patient along with the patient's heart rate information. This combined group of data will be unique to each individual being tested (due to the biometric and heart rate information) and can be uniquely linked to each individual.

All readings and identification data are bundled in an encrypted data packet that can be sent securely via digital media (Internet, Intranet, Extranet, Virtual Private Network, Local Area Network, Wide Area Network, etc.). The portable processor can be configured to remotely (example is from a patient's home) transmit all relevant data (patient pulse oximeter readings along with identification data) to a central data repository accessible via the Internet or other data connection (Intranet, Extranet, VPN, LAN, WAN, etc.). This central data repository can be accessed as a web application, ASP Model (Application Service Provider), or can be synchronized with one or multiple client workstations or other client devices (Personal Digital Assistants (PDA), WAP (Wireless Access Protocol) enabled phones, etc.) that are running client-side software.

The following process can be employed at the test site.

Employee biometric information is taken to verify the identity of the person administering the test. This will allow the IDTF (Independent Diagnostic Testing Facility) to validate that only people qualified to give certain tests are performing the tests. It will also identify the person administering the tests for fraud purposes.

The employee will also have their photograph taken to further ensure that the person administering the test is the person who is qualified and authorized to administer the test. This is done, once again, to reduce/eliminate fraud. This step will be done in tandem with the biometric readings taken on the employee to validate the employee.

A test administrator central repository will be developed based on the unique test administrators entered into the system. This central repository will be checked with each test to make sure that the employee is a valid, test administrator to administer the test. Different levels of certification and qualification will be required for employees to be eligible to administer certain types of tests. The IDTF (Independent Diagnostic Testing Facility) will house the central database of all employees qualified to administer tests. The IDTF will provide access rights based on the qualification of different levels of employees Qualification will also be based on a valid driver's license, a criminal background check and clearance (immediate and periodic checks), and clinical license and certification (i.e. RCP (Repiratory Care Practitioner), RN (Registered Nurse), Sleep Technician, etc.). This data will also be housed in the central data repository and may be necessary when performing certain tests (OSA, etc.).

To begin a test an initialization procedure can be followed:

Step 1: The dealer's employee/test administrator enters, downloads or transfers required information, i.e. patient demographic, insurance & physician information, prior to taking the patient identification system 10 to the test site. Software may be utilized in the portable processor 12.

Step 2: Once with the patient (home or remote location), the test administrator chooses the test to be performed on the patient, i.e. Oximetry, Sleep Apnea pre-screen, etc.

Step 3: The test administrator will then take his/her own biometric (could also take their own photograph) by placing the first sensor on his/her finger. The portable processor will record the employee's biometric information (and photograph if relevant) and will prepare itself for step 4.

Step 4: The test administrator will have 5 minutes (or other relevant time frame depending on the test to be performed, OSA, Oximetry, OSA pre-screen, etc.) to take a photograph and biometric measurement of the patient on whom the test will be performed. The reason for imposing a time limitation on the patient setup is to avoid a company or person taking a biometric of an authorized employee but then having another do the actual patient setup (employee substitution). At precisely the same time as the photograph, the patient's heart rate is taken on the finger sensor. Additionally, a separate sensor can be in place on the patient's ear (or elsewhere) to record a separate instance of the patient's heart rate. This heart rate will be compared with the heart rate taken from the finger sensor to validate that the readings are from the same person. The illustrative second sensor 16 is equipped with an LCD (Liquid Crystal Display) or LED (Light Emitting Diode) to display a randomly generated alphanumeric number or other identifier (generated by this device or software) to further validate the patient's identity. The random identifier is generated when the picture is taken and will serve 2 purposes. This random identifier will be displayed in plain view on the ear sensor to be included in the photograph of the patient. Additionally, the software on the portable processor 12 can digitally sign the data with the same random identifier to further validate the patient identity.

Step 5: Portable processor 12 will then connect with the central test administrator database (dial-up modem, broadband, VPN, Intranet, Extranet, etc.). The portable processor 12 device ID is checked to ensure the device is valid based on the dealer to which it has been assigned. Next, the employee biometric will be compared to the biometric in the test administrator database, for that dealer, to ensure that the employee is valid, and is authorized to conduct this test. This can be illustratively done in real time. If the person is not authorized to conduct the test, the portable processor 12 will notify the employee that they are not authorized to conduct the test and the process will not be permitted to continue. Illustratively, to perform a test on the patient a new test must be established and initialized as described above. The benefit to this procedure is that the exact person conducting the test is known and fraud can be substantially reduced. Once the test administrator has been verified and approved, the patient biometric information is recorded. This will allow the IDTF to track the expected patient test submissions within a prescribed time limit (i.e. 24-36 hours). Additionally, this will allow the IDTF to compare the patient data to patient data already existing in the central repository. If duplicate patient biometric information is recorded, but not expected by the system (i.e. Medicaid required qualifying patients to be re-tested every 2 years, etc.) then IDTF officials will be notified and the patient record (along with the HME Dealer record) will be highlighted for review. If fraud is detected (i.e. the HME Dealer is intentionally submitting false results or duplicate qualifying results) then the appropriate authorities will be contacted. Providing the test administrator is qualified and the patient data record is in order, an approval code will be transmitted to the remote device and the test will be initialized. At this point, the test administrator may disconnect the device from the central repository and may leave the remote device with the patient. The patient may begin the actual test at any time they wish.

Step 6: The patient will connect the finger sensor to begin the test. The patient biometric is then compared with the patient biometric data recorded during the initialization step. Throughout the course of the test, continuous and/or random biometric patient validation tests will be conducted in conjunction with the oximetry tests being conducted. If at any point a patient's biometric information is found to be different from the patient biometric information recorded during the initialization phase, the test will be invalidated and can signal for immediate conclusion.

Step 7: Once the test has been completed, the test administrator can return to the patient's location to confirm process completion (device will indicate to employee that test is complete and data is ready to transmit. Data is unalterable by the employee) and to transfer the test results to the central data repository. The test administrator will be able to use any type of connectivity to connect to the central data repository (dial-up modem, broadband, wireless, VPN, Extranet, Intranet, etc.). Once connected and authenticated the patient test data is transferred to the central data repository and associated with the patient record. The test data is then purged from the remote device and the device is now ready to be initialized for another patient test.

Step 8: The biometric test data can be compared automatically or manually to ensure patient identity. Assuming there is no discrepancy, the test results along with the photograph are illustratively sent to a physician and dealer.

Step 9: Once a patient's test results have been submitted and validated to that patient the patient data is stored in the central data repository. Patient test results, along with the patient's photograph, are sent to the physician for validation. Upon review and validation of the patient results and photograph the physician approves the results. This information is then used to auto populate the CMN (Certificate of Medical Necessity) or Electronic Certificate of Medical Necessity. The CMN can be electronically transmitted and may be signed by the doctor electronically (electronic signature). Once the doctor has signed the CMN, the CMN is automatically transmitted to the appropriate entities (i.e. IDTF, HME Dealer, etc.). The doctor will have the ability to confirm patient identity through the patient data transmitted on the CMN as well as via the patient photograph which can be attached on the transmission to the doctor (and HME Dealer). The doctor can either accept or reject the test results (and CMN form). To accept the results, the doctor will sign the form (electronically and/or manually) and will transmit the completed CMN form (electronically and/or manually) to the appropriate entitie(s) (HME Dealer). To reject the results or CMN the doctor will select the appropriate entry digitally or manually and will notify the appropriate entities(s) (HME Dealer, IDTF). If any discrepancies are found in the patient data record or patient results that the doctor does not agree with, the doctor will have the ability to reject the results and indicate and describe the appropriate reason(s). If the IDTF is contacted by the doctor and fraud is detected, the appropriate authorities will be contacted.

It is important to note that the CMN forms and test results are un-alterable.

Although the current system has been developed specifically related to pulse oximeter readings and unique patient identification, the applicability of this system is far reaching. This system has utility as related to any home healthcare and/or remote patient monitoring system (fetal monitoring, OSA (Obstructive Sleep Apnea: www.sleep-solutions.com) studies, etc.) as this system provides a way to specifically identify an individual patient with the results and readings being recorded and submitted. This system provides a data trail and unique signature to allow any type of home healthcare procedure to specifically identify the appropriate individual with their readings. The system can be set to work in relation in prescreening studies for OSA. Alternative equipment may also be incorporated into this system for additional testing such as a thermistor which could be used for OSA prescreening.

While the disclosure is susceptible to various modifications and alternative forms, specific exemplary embodiments thereof have been shown by way of example in the drawings and have herein been described in detail. It should be understood, however, that there is no intent to limit the disclosure to the particular forms disclosed, but on the contrary, the intention is to cover all modifications, equivalents, and alternatives falling within the spirit and scope of the disclosure as defined by the appended claims.

There is a plurality of advantages of the present invention arising from the various features of the patient identification system and associated method described herein. It will be noted that alternative embodiments of the patient identification system and associated method of the present invention may not include all of the features described yet still benefit from at least some of the advantages of such features. Those of ordinary skill in the art may readily devise their own implementations of a patient identification system and associated method that incorporate one or more of the features of the present invention and fall within the spirit and scope of the present invention as defined by the appended claims.

What is claimed is:

1. A method of identifying a person in a healthcare related transaction, including the steps of:
   (a) measuring fingerprint data from a person;
   (b) measuring non-fingerprint biometric data from the person at a first location in a finger region of the person at the same time the fingerprint data is being measured;
   (c) measuring the same non-fingerprint biometric data being measured at the first location at a second location at the same time the fingerprint data and the biometric data at the first location are being measured;
   (d) displaying a randomly generated identifier at the second location at the same time the fingerprint data and the non-fingerprint biometric data are being measured;
   (e) capturing the fingerprint data and the non-fingerprint biometric data measured at the first and second locations;
   (f) capturing a visual representation while the fingerprint and non-fingerprint biometric measurements are being made that includes the person's facial characteristics, the randomly generated identifier, and both of the biometric measurement locations; and
   (g) associating the visual representation with information based upon data captured from the fingerprint and non-fingerprint biometric measurements at the same time the visual representation was created to create a dataset unique to the person only at the time the visual representation was captured.

2. A method as recited in claim 1 wherein the second location is different than the first location.

3. A method as recited in claim 1 wherein the biometric parameter being measured includes a pulse measurement.

4. A method as recited in claim 3 wherein the visual representation is further associated with the date and time at which the biometric data and visual representation were captured.

5. A method as recited in claim 1 where the fingerprint data is measured on the same finger of the person from which the first biometric measurement is taken.

6. A method as recited in claim 1 wherein the randomly generated identifier is photographed.

7. A method as recited in claim 1 further including the step of associating the visual representation with the randomly generated identifier to create the dataset unique to the person only at the time the visual representation was captured.

8. A method as recited in claim 1 further including the step of capturing identification information from the person.

9. A method of identifying a person in a healthcare related transaction, including the steps of:
   (a) measuring a biometric parameter at a first location in a finger region of a person;
   (b) measuring the same biometric parameter at a second location at the same time biometric data is being measured at the first location;
   (c) capturing the biometric data measured at the first and second locations;

(d) displaying a randomly generated identifier at the second location at the same time the biometric data at the first and second locations is being measured;

(e) capturing a visual representation while measurements are being made at the first and second locations that includes the person's facial characteristics, the randomly generated identifier, and both of the biometric measurement locations; and (f) associating the visual representation with information based upon data captured from the first and second locations at the same time the visual representation was created to create a dataset unique to the person only at the time the visual representation was captured.

10. A method as recited in claim 9 wherein the date and time the visual representation was taken are further associated with the visual representation and the information based upon data captured from the first and second locations.

11. A method as recited in claim 9 further including the step of measuring fingerprint parameter at the finger region of the first location during the period the biometric data is being measured at the first and second locations, and further including the step of associating the fingerprint data with the visual representation.

12. A method of substantiating a biometric measurement by associating it with a photographic image, including the steps of:
   (a) measuring a predetermined biometric parameter of a person with a sensing device at both a first and a second location;
   (b) displaying a randomly generated identifier at the second location at the same time the predetermined biometric data at the first and second locations is being measured;
   (c) capturing a visual representation at the same time as the biometric data is being measured, including the randomly generated identifier, data about the facial characteristics of the person and the sensing device; and
   (d) associating the captured visual representation with the randomly generated identifier and the biometric data to insure the visual representation has been taken from the same person from whom the biometric data was captured.

13. A method as recited in claim 12 wherein the visual representation is associated with the biometric parameter at the date and time the biometric data is captured to create a unique dataset.

14. A method as recited in claim 13 wherein the biometric parameter is a fingerprint.

15. A method as recited in claim 12 wherein the biometric parameter is retinal scan.

16. A method of substantiating a biometric measurement by associating it with a photographic image, including the steps of:
   (a) measuring a biometric parameter of a person with a sensing device at both a first and a second location during a first time period;
   (b) displaying a randomly generated identifier at the second location at the same time the biometric data at the first and second locations is being measured;
   (c) capturing a visual representation of the person at the same time as the biometric parameter is being measured during the first time period, including the randomly generated identifier and data about the facial characteristics of the person;
   (d) associating the captured visual representation with the randomly generated identifier and the biometric parameter captured during the first time period to create a dataset unique to the person only at the time the visual representation was captured; and
   (e) measuring the biometric parameter at a time subsequent to the first time period and using the unique dataset to confirm that the biometric parameter measured at the subsequent time is from the same person from whom the biometric parameter measured during the first time period.

17. A method as recited in claim 16 wherein the biometric parameter is fingerprint data.

18. A method as recited in claim 16 wherein the biometric parameter is retinal data.

19. A method of identifying a person in a healthcare related transaction, including the steps of:
   (a) measuring non-fingerprint biometric data from a person at a first location proximal to a finger of the person during a first period of time;
   (b) measuring the same non-fingerprint biometric parameter at a second location of the person at the same time the non-fingerprint biometric parameter is being measured at the first location, the second location being spaced from the first location;
   (c) displaying a randomly generated identifier at the second location at the same time the biometric data at the first and second locations is being measured;
   (d) recording fingerprint information from the finger at the same time the non-fingerprint biometric measurement is being taken at the first and second locations;
   (e) capturing a visual representation while measurements are being made at the first and second locations that includes the facial characteristics of the person, the randomly generated identifier, and both of the biometric measurement locations;
   (f) associating the visual representation with the randomly generated identifier and the information based upon data captured from the first and second locations to create a dataset unique to the person only at the time the visual representation was captured; and
   (g) measuring the fingerprint information subsequent to the first period of time and utilizing the unique dataset to confirm that the fingerprint information taken at the subsequent time is from the same person from whom the fingerprint information was recorded during the first period of time.

20. A method as recited in claim 19 wherein data related to the date and time the visual representation was taken during the first time period is associated with the visual representation and used to create a unique dataset, and the unique dataset is used to insure that the fingerprint information taken at the subsequent time is from the same person from whom the fingerprint information was taken during the first period of time.

21. A method of associating a person's fingerprint and facial identification data, including the steps of:
   (a) capturing fingerprint data from a person;
   (b) creating a randomly generated identifier;
   (c) simultaneously with the capture of the fingerprint, capturing data representative of the person's visual facial characteristics and the randomly generated identifier; and
   (d) intermingling the data representative of the person's facial characteristics with,
      (i) the fingerprint data captured at the time data representative of the person's facial characteristics was captured, and
      (ii) the randomly generated identifier; to form a data set unique to the person.

* * * * *